United States Patent [19]

Tanaka et al.

[11] Patent Number: 4,683,288

[45] Date of Patent: Jul. 28, 1987

[54] POLYMER AND ITS PRODUCTION

[75] Inventors: Motoaki Tanaka, Saitama; Yasuaki Ogawa, Osaka; Tsutomu Miyagawa; Toshio Watanabe, both of Saitama, all of Japan

[73] Assignees: Waco Pure Chemical Ind. Inc.; Takeda Chemical Industries, Ltd., both of Osaka, Japan

[21] Appl. No.: 751,671

[22] Filed: Jul. 3, 1985

[30] Foreign Application Priority Data

Jul. 6, 1984 [JP] Japan .................................. 59-140356

[51] Int. Cl.$^4$ ............................................. C08G 63/04
[52] U.S. Cl. ...................................... 528/361; 528/354
[58] Field of Search ................ 528/354, 355, 357, 361

[56] References Cited

U.S. PATENT DOCUMENTS

| | | | |
|---|---|---|---|
| 2,362,511 | 11/1939 | Teeters et al. | 260/72 |
| 2,703,316 | 3/1955 | Schneider | 528/354 |
| 3,468,853 | 9/1969 | Schmitt et al. | 528/357 X |
| 3,531,561 | 9/1970 | Trehu | 528/354 X |
| 3,636,956 | 1/1972 | Schneider | 528/354 X |
| 3,839,297 | 10/1974 | Wasserman et al. | 528/354 X |
| 4,137,921 | 2/1979 | Okuzumi et al. | 528/354 X |
| 4,273,920 | 6/1981 | Nevin | 528/361 |

OTHER PUBLICATIONS

Asahara, et al., "Production of Polyglycolide.Lactide and Properties of the Product", J. Chem. Soc. Japan, 65 (1965), No. 5, pp. 983–986.

*Primary Examiner*—Earl Nielsen
*Attorney, Agent, or Firm*—Wegner & Bretschneider

[57] ABSTRACT

A polymer or copolymer of lactic acid and/or glycolic acid which has a weight-average molecular weight of not less than about 5,000 and a dispersity of about 1.5 to 2 is advantageously used as a biodegradable polymer or copolymer for medical preparation.

13 Claims, No Drawings

POLYMER AND ITS PRODUCTION

The present invention relates to a polymer of lactic acid or glycolic acid, a copolymer of lactic acid and glycolic acid and a method for producing the polymer or the copolymer by a polycondensation reaction in the presence of a solid inorganic acid catalyst.

In recent years, degradable polymers have attracted a good deal of attention, for example, as a readily degradable polymer serving to mitigate environmental pollution by plastics and also as a biodegradable polymer for medical use.

As the method for producing a copolymer of lactic acid and glycolic acid, there is mentioned a method disclosed in U.S. Pat. No. 4,273,920. In the U.S. patent, it is stated that the copolymer being substantially free of polymerization catalyst is obtained by reacting lactic acid with glycolic acid in the presence of a readily removable strong acid ion-exchange resin, and removing the resin therefrom.

However, the copolymers produced by the above-described method all exhibit a dispersity in molecular weight as high as nearly 3 or more and in use cause a great complexity in factors involved in solubility and other aspects, thus causing major problems in controlling such factors. Therefore, they cannot be said to be very useful, when they are used, for example, as a biodegradable polymer for medical use. In addition, this method allows the strong acid ion exchange resin being used as a polymerization catalyst to deteriorate due to heat during a polycondensation reaction under heating and to become dissolved in the resulting copolymer, thereby contributing to the development of coloration of the copolymer. Once the copolymer becomes colored, it is difficult to eliminate such coloration and it is practically impossible to remove completely such coloration; the coloration shows that the catalyst, i.e. strong acid ion-exchange resin, cannot be completely removed. It goes without saying that such coloration not only diminishes the values as an article of commerce but also is in the undesirable, because it is attributed to impurities.

The present inventors conducted intensive research, and found a method for producing a polymer of lactic acid or glycolic acid and a copolymer of lactic acid and glycolic acid, which are effective and free from the above-mentioned disadvantages. Based on this finding and further research, the present inventors have completed the present invention.

The present invention is directed to:

(1) a polymer or copolymer of lactic acid and/or glycolic acid, which has a weight-average molecular weight of not less than about 5,000 and a dispersity of about 1.5 to 2, and (2) in a method for producing a polymer or copolymer of lactic acid and/or glycolic acid by subjecting lactic acid and/or glycolic acid to a polycondensation reaction, an improvement which comprises employing a solid inorganic acid catalyst as a polycondensation catalyst.

In the method of the present invention, lactic acid and/or glycolic acid are/is employed, as the starting materials, in the form of crystals, powders or granules as such, or in the form of an aqueous solution. The concentration of the solution is arbitrarily selected, preferably as high as possible, and more preferably not lower than about 85% (w/w).

As the lactic acid and/or glycolic acid units employed in the present invention as a starting material, low molecular polymer of lactic acid or glycolic acid or low molecular copolymer of lactic acid and glycolic acid may be used.

As the low molecular polymer of lactic acid or glycolic acid, there are mentioned an oligomer (e.g. dimer, trimer, etc.) of lactic acid, an oligomer (e.g. dimer, trimer, etc.) of glycolic acid and so on.

As the low molecular polymer or copolymer as a starting material, there can serve those which is produced by subjecting lactic acid and/or glycolic acid to polycondensation reaction in the absence of a catalyst under for example about 100° to 150° C./350 to 30 mmHg for more than about 2 hours, normally about 2 to 10 hours, more preferably while increasing the temperature and the degree of reduced pressure stepwise from about 105° C./350 mmHg to 150° C./30 mmHg for about 5 to 6 hours, to thereby remove water. In this process, a low molecular polymer or copolymer of molecular weight of about 2000 to 4000 is obtained.

Furthermore, as the low molecular copolymers, there are mentioned, for example, those obtainable by the methods described in Kogyo Kagaku Zasshi (Journal of the Chemical Society of Japan), vol. 68, pp. 983–986 (1965), i.e. lactic acid and glycolic acid are reacted at a normal atmospheric pressure and in the absence of a catalyst at 202° C. for 6 hours, or U.S. Pat. No. 2,362,511, i.e. lactic acid and glycolic acid are reacted at a temperature of 200° C. holding the mixture at that temperature for a period of about 2 hours and subsequently continuing the heating for another period of about ½ hour under vacuum.

The ratio of lactic acid to glycolic acid in the copolymer, when the object compound is a copolymer of these compounds, is preferably about 50 to 95 weight % of lactic acid and about 50 to 5 weight % of glycolic acid, more preferably about 60 to 95 weight % of lactic acid and about 40 to 5 weight % of glycolic acid, and still more preferably about 60 to 85 weight % of lactic acid and about 40 to 15 weight % of glycolic acid. The ratio is especially preferable about 75±2 mol % of lactic acid and about 25±2 mol % of glycolic acid.

In the present method, a solvent may be employed, when the starting materials are crystals, powders or granules, to dissolve these compounds. As the solvents, there are mentioned, for example, water, methanol, ethanol, acetone, etc.

The solid inorganic acid catalyst, which is usable in the present invention, includes, for example, acid clay, activated clay, bentonite, kaolin, talc, aluminum silicate, magnesium silicate, alumina bolia, silicic acid, etc. These can all be used, either solely or as a mixture of not less than two kinds thereof, and each is employed as such or after being washed with, for example, hydrochloric acid of a concentration of 5 to 20% to remove metal ions, if necessary.

The amount of the solid inorganic acid catalyst used in the present method is normally about 0.5 to 30% w/w, preferably about 1 to 20% w/w, based on the total amount of lactic acid and glycolic acid. The catalyst can be used in one or several portions.

The catalyst may be added to the reaction system in the course of the reaction.

The present method is preferably carried out under heating and reduced pressure. The heating is carried out by heating the reaction system at about 150° to 250° C., preferably about 150° to 200° C. The reduced pressure is normally about 30 to 1 mmHg, preferably about 10 to 1 mmHg. The reaction time of the present polycondensation reaction is normally not less than about 10 hours, preferably about 10 to 150 hours, more preferably about 10 to 100 hours.

Referring to the reaction steps and conditions in the present method when lactic acid and/or glycolic acid are employed as the starting materials, the following are preferred: A heating reaction under reduced pressure may be allowed to proceed at about 100° to 150° C./350 to 30 mmHg for not less than about 2 hours, normally about 2 to 10 hours, for example, for about 5 to 6 hours while increasing the temperature and the degree of reduced pressure stepwise to about 105° C./350 mmHg to 150° C./30 mmHg, to thereby remove water, followed by a dehydration polycondensation reaction at about 150° to 200° C./10 to 1 mmHg for not less than about 10 hours; normally up to about 100 hours may be adequate.

When the low molecular polymer or copolymer is employed as the starting material, preferable reaction conditions are as follows: A dehydration polycondensation reaction is carried out at about 150° to 200° C./10 to 1 mmHg for not less than about 10 hours, normally up to about 100 hours may be adequate.

After the termination of the reaction, the objective polymer or copolymer can be readily obtained by removing the used solid inorganic acid catalyst. The solid acid catalyst of the present invention can be easily removed, for example by filtration with suction using ordinary qualitative filter paper. Through mere hot filtration of the reaction solution or filtration after dissolution of the polymer or copolymer in a suitable solvent such as methylene chloride, dichloroethane, chloroform, acetone, in an amount of equal to about 10-times that of the polymer or copolymer, whereupon no subsequent treatment is required to be carried out in the former case where the reaction solution is filtered as such and the employed solvent is concentrated or distilled off in the latter case where the reaction solution is filtered after being dissolved in a solvent. If desired, separation may be performed in accordance with a conventional method, for example, by pouring the filtered reaction solution, either directly or in the form of a concentrated filtrate in the case of a solvent being used, into a large amount of a precipitant, and if further required, purification may be carried out by reprecipitation, etc.

According to the present invention, there can be formed the polymer or copolymer consisting of lactic acid and/or glycolic acid units having a weight-average molecular weight of not less than about 5,000, preferably about 5,000 to 30,000, and the polymer or copolymer has a dispersity of about 1.5 to 2. Furthermore, the polymer or copolymer is colorless to almost white.

As the polymer or copolymer of the present invention has a low degree of dispersity, the distribution of the molecular weight of the polymer or copolymer is not wide.

Furthermore, as the solid inorganic acid catalyst is insoluble in the polymer or copolymer and in a solvent, the catalyst is completely removed from the reaction product and the resulting polymer or copolymer is free of coloration due to the catalyst.

The polymer or copolymer obtained by the present method can be utilized mainly as a base for drug preparation. For example, they can be advantageously utilized by incorporating steroid hormones, peptide hormones or anti-tumor agents, etc. into them to process into an embedded type of microcapsule type of controlled release preparations or by preparing fine particles containing an anti-tumor agent to process into a therapeutic agent for embolization.

The Experiment Examples and Examples are described below to illustrate the present invention in more detail.

EXPERIMENT EXAMPLE 1

To 160 g (1.5 mole as lactic acid) of a 85% aqueous solution of lactic acid was added 6.8 g of a solid inorganic acid catalyst, and heating under reduced pressure was carried out for 6 hours under the stepwise varying conditions of 100° to 150° C./350 to 30 mmHg under a stream of nitrogen gas to remove the resulting water. Subsequently, 6.8 g of the solid acid catalyst was added additionally, followed by a dehydration polycondensation reaction at 175° C./5 mmHg for 72 hours.

Shown in Table 1 is the relationship between reaction time and weight-average molecular weight attained and its dispersity in the production of lactic acid polymers.

Also shown in Table 1 for the purpose of comparison are the results obtained with Dowex 50 (a cross-linked polystyrene resin, Dow Chemical Co., U.S.A.), a strongly acidic ion-exchange resin being commercially available, which was used as a polymerization reaction.

The weight-average molecular weight and dispersity $$\left( \text{dispersity} = \frac{\text{weight-average molecular weight}}{\text{number-average molecular weight}} \right)$$

in the present specification were measured by gel permeation chromatography utilizing standard polystyrene with known molecular weight.

TABLE 1

| | Type of polymerization catalysts and molecular weight attained and its dispersity | | | |
|---|---|---|---|---|
| Catalyst: | Acid clay | Aluminum silicate | Activated clay | Dowex 50 W |
| Added amount (1) | 6.8 g | 6.8 g | 6.8 g | 6.8 g |
| Added amount (2) | 6.8 g | 6.8 g | 6.8 g | 6.8 g |
| 12 hours of reaction time | — | 6,200 (1.71) | 5,000 (1.63) | — |
| 24 hours of reaction time | 8,900 (1.88) | 11,200 (1.66) | 8,800 (1.61) | 9,100 (2.43) |
| 36 hours of reaction time | 16,600 (1.72) | 15,600 (1.65) | 12,700 (1.62) | 11,400 (2.63) |
| 48 hours of reaction time | — | 19,100 (1.65) | 16,700 (1.50) | 14,900 (2.80) |
| 60 hours of reaction time | 26,500 (1.73) | 22,500 (1.66) | 19,900 (1.67) | 17,800 (2.81) |

TABLE 1-continued

| | Type of polymerization catalysts and molecular weight attained and its dispersity | | | |
|---|---|---|---|---|
| Catalyst: | Acid clay | Aluminum silicate | Activated clay | Dowex 50 W |
| 72 hours of reaction time | 29,300* (1.77) | 25,800 (1.66) | 23,700 (1.81) | 20,200 (2.80) |
| Appearance of the polymer** | Almost white | Almost white | Almost white | Dark brown (the color deepens with time) |

Note:
*Reaction time of nearly 65 hours.
**Each of the polymers obtained after the respective reaction time was dissolved in methylene chloride of the volume four times that of the polymer, and the solution was filtered using Toyo Filter Paper No. 131 [Toyo Roshi Co., Ltd., Japan] to remove the catalyst, and then concentrated to distill off the solvent; the resulting polymers were examined in accordance with JIS K 8004-2 (namely, about 3 g of the specimen is taken on a watch glass, which is placed on a sheet of white paper and examined.).

In the Table 1, the added amount (1) of catalyst and the added amount (2) of catalyst denote an initially added amount of catalyst and an amount of catalyst additionally added at the time of the polycondensation reaction at 175° C./5 mmHg after removal of water, respectively while the reaction time means that at 175° C./5 mmHg. In the table, the parenthesized value beneath the molecular weight attained indicates a dispersity.

As is clear from Table 1, the present invention permits readily the production of high molecular weight polymer with a weight-average molecular weight of not less than about 5,000 being almost free from polymerization catalyst; wherein the resulting polymers show that colored appearance is hardly observed and the polymers have dispersity of not more than 2, with the polymerization reaction rate being evidently promoted by the addition of the catalyst.

EXPERIMENT EXAMPLE 2

After 160 g (1.5 mole) of a 85% aqueous solution of lactic acid and 38 g (0.5 mole) of glycolic acid were mixed, 8.7 g of a solid acid catalyst was added to the mixture, and heating under reduced pressure was carried out at 100° to 150° C./350 to 30 mmHg under a stream of nitrogen gas for 6 hours to remove the distilled water. Subsequently, 8.7 g of the solid acid catalyst was added additionally, followed by a dehydration condensation reaction at 175° C./6 to 5 mmHg for 72 hours.

Shown in Table 2 is the relationship between reaction time and weight-average molecular weight attained in the production of copolymers of lactic acid and glycolic acid.

Also, shown in Table 2 for the purpose of comparison are the results obtained with a strongly acidic ion-exchange resin (Dowex 50W) which was used as a polymerization catalyst.

TABLE 2

| | Type of polymerization catalysts and molecular weights attained | | | |
|---|---|---|---|---|
| Catalyst: Type | Acid clay | Aluminum silicate | Activated clay | Dowex 50W |
| Added amount (1) | 8.7 g | 8.7 g | 8.7 g | 8.7 g |
| Added amount (2) | 8.7 g | 8.7 g | 8.7 g | 8.7 g |
| 12 hours of reaction time | — | 5,100 (1.72) | — | — |
| 24 hours of reaction time | 12,600 (1.72) | 11,700 (1.72) | 10,200 (1.69) | 10,500 (2.47) |
| 36 hours of reaction time | 18,600 (1.73) | 17,800 (1.74) | 16,100 (1.65) | 14,400 (2.44) |
| 48 hours of reaction time | 22,900 (1.65) | 22,000 (1.64) | 20,400 (1.64) | 18,900 (2.46) |
| 60 hours of reaction time | 25,400 (1.68) | 25,800 (1.68) | 22,800 (1.63) | 22,200 (2.47) |
| 72 hours of reaction time | 27,900 (1.76) | 28,600 (1.66) | 26,000 (1.63) | 25,300 (2.76) |
| Appearance of the polymer* | Almost white | Almost white | Almost white | Dark brown (the color deepens with time) |

Note:
*Each of the polymers obtained after the respective reaction time was dissolved in methylene chloride of the volume four times that of the polymer, and the solution was filtered using Toyo Filter Paper No. 131 to remove the catalyst, and then, concentrated to distill off the solvent; the resulting polymers were examined in accordance with JIS K 8004-2 (namely, about 3 g of the specimen is taken on a watch glass, which is placed on a sheet of white paper and examined.).

In the Table 2, the added amount (1) of catalyst and the added amount (2) of catalyst denote an initially added amount of catalyst and an amount of catalyst additionally added at the time of the polycondensation reaction at 175° C./5 mmHg after removal of water, respectively, while the reaction time means that at 175° C./5 mmHg. In the Table 2, the parenthesized value beneath the molecular weight attained indicates dispersity.

As is clear from Table 2, the present invention can permit readily the production of high molecular weight lactic acid glycolic acid copolymers with a weight-average molecular weight of not less than about 5,000 being almost free from polymerization catalyst, in the resulting copolymers colored appearance is hardly observed, and dispersity is as small as and not more than 2, with the polymerization reaction rate being evidently promoted by the addition of the catalyst.

Furthermore, analysis of nuclear magnetic resonance spectrometry on said resulting copolymer of the present invention in $CDCl_3$ solution indicates the following content of lactic acid and glycolic acid.

| Copolymer ratio of the present copolymer (lactic acid:glycolic acid) | | | |
|---|---|---|---|
| | | | mol % (weight %) |
| | | Catalyst | |
| Reaction time | Acid Clay | Aluminum silicate | Activated Clay |
| 12 hours | —— | 75.5:24.5 (79.3:20.7) | —— |
| 24 hours | 75:25 (78.8:21.2) | 75:25 (78.8:21.2) | 75.5:24.5 (79.3:20.7) |
| 36 hours | 75:25 (78.8:21.2) | 75:25 (78.8:21.2) | 75:25 (78.8:21.2) |
| 48 hours | 75:25 (78.8:21.2) | 76:24 (79.7:20.3) | 75:25 (78.8:21.2) |
| 60 hours | 75.5:24.5 (79.3:20.7) | 75.5:24.5 (79.3:20.7) | 76:24 (79.7:20.3) |
| 72 hours | 75.5:24.5 (79.3:20.7) | 75.5:24.5 (79.3:20.7) | 75.5:24.5 (79.3:20.7) |

EXAMPLE 1

Placed in a four-necked flask equipped with a thermometer, condenser and inlet tube for nitrogen gas were 160 g of a 85% aqueous solution of lactic acid and 13.6 g of acid clay, and heating under reduced pressure was carried out under a stream of nitrogen gas over the period of 6 hours, while increasing the internal temperature and the degree of internal reduced pressure stepwise from 105° C. and 350 mmHg to 150° C. and 30 mmHg, and then the resulting water was removed. Successively, heating was conducted under reduced pressure of 3 mmHg and at the internal temperature of 175° C. for 50 hours. The reaction solution was cooled to room temperature, and 400 ml of methylene chloride was added to it, followed by stirring to a solution. Then, the acid clay was removed by filtration using Toyo Filter Paper No. 131, and the filtrate was concentrated to dryness to give 100 g of an almost colorless polymer, which has a weight-average molecular weight of 22,000 and a dispersity of 1.75.

In order to determine the remaining catalyst in the resulting copolymer, a specimen of the copolymer was weighed out onto a dish of platinum and subjected to a fusing treatment with sodium carbonate, and then aluminum and silicon were determined colorimetrically by application of the aluminon method and molybdenum blue method, with the result that neither of the metals was detected, leading to the conclusion that no contamination by the catalyst was observed.

EXAMPLE 2

A reaction was carried out in the manner of Example 1, except that 27.2 g of aluminum silicate was used as a catalyst, and there was obtained 92 g of an almost colorless polymer, which has a weight-average molecular weight of 21,900 and a dispersity of 1.70. Similar results were obtained when kaolin and talc were used in place of aluminum silicate as a catalyst.

In order to determine the remaining catalysts in the resulting copolymers, detection of the remaining catalysts was carried out in a manner of Example 1, with the result that there was no contamination of catalysts observed.

EXAMPLE 3

In the manner of Example 1, 160 g of a 85% aqueous solution of lactic acid was used, but 6.8 g of activated clay was charged in place of acid clay, whereupon after removal of the resulting water, a heating reaction was conducted at the internal pressure of 5 mmHg and at the internal temperature of 185° C. for 96 hours to give 90 g of an almost white polymer. The resulting polymer has a weight-average molecular weight of 29,600 and a dispersity of 1.85.

In order to determine the remaining catalyst in the resulting polymer, detection of the remaining catalyst was carried out in the manner of Example 1, with the result that there was no contamination of catalyst observed.

EXAMPLE 4

A reaction was conducted in the manner of Example 1, except that 160 g of a 85% aqueous solution of lactic acid, 38 g of glycolic acid and 17.4 g of activated clay were used, and there was obtained 122 g of an almost white copolymer, which has a weight-average molecular weight of 20,100 and a dispersity of 1.70, and shows a copolymerization composition of lactic acid and glycolic acid of 76 mol %: 24 mol % (79.7 weight %: 20.3 weight %).

In order to determine the remaining catalyst in the resulting copolymer, detection of the remaining catalyst was carried out in the manner of Example 1, with the result that there was no contamination of catalyst observed.

EXAMPLE 5

Charged were 191 g of a 85% aqueous solution of lactic acid, 17.5 g of glycolic acid and 9 g of acid clay, and after removal of the distilled water, a heating reaction was carried out at the internal pressure of 3 mmHg and at the internal temperature of 170° C. for 96 hours to give 130 g of an almost white copolymer. The resulting copolymer has a weight-average molecular weight of 28,100 and a dispersity of 1.73, and a copolymerization composition of lactic acid and glycolic acid of 89 mol %:11 mol % (90.9 weight %:9.1 weight %).

The similar results were obtained, when the similar reaction was carried out with aluminum silicate, bentonite and kaolin being used as a catalyst instead.

Determination of remaining catalist was conducted in the manner of Example 1, with the result that there was no contamination of catalysts observed.

EXAMPLE 6

146 g of a 93% aqueous solution of lactic acid and 38 g of glycolic acid was used, a heating reaction was conducted at the temperature of 202° C. for 6 hours, whereby a copolymer with a weight-average molecular weight of 2,700 and a composition of lactic acid and glycolic acid of 75 mol %:25 mol % was obtained. Weighed in the same polymerization apparatus as used in Example 1 were 100 g of this copolymer and 10 g of acid clay, and heating was carried out under reduced pressure of 5 mmHg at internal temperature of 180° C. for 50 hours. The reaction solution was cooled to room temperature, and 500 ml of methylene chloride was added to it, followed by stirring to a solution. Then, the acid clay was removed by filtration using Toyo Filter Paper No. 131 and the filtrate was concentrated to dryness to give 82 g of an almost colorless polymer, which showed a weight-average molecular weight of 23,700 and a dispersity of 1.73, and a copolymerization composition of lactic acid and glycolic acid of 75 mol %:≃mol % (78.8 weight %:21.2 weight %).

In order to determine the remaining catalyst in the resulting polymer, detection of the remaining catalyst was carried out in the manner of Example 1, with the result that there was no contamination of catalyst observed.

EXAMPLE 7

A reaction was conducted in the manner of Example 6, except that 97 g of lactic acid dimer (Lactic acid lactate) and 54 g of glycolic acid dimer (Glycologlycolic acid) and 7.5 g of acid clay were used, and there was obtained 98 g of an almost white copolymer, which has a weight-average molecular weight of 21,000 and a dispersity of 1.75, and a copolymerization composition of lactic acid and glycolic acid of 59.5 mol %:40.5 mol % (64.6 weight %:35.4 weight %).

In order to determine the remaining catalyst in the resulting copolymer, detection of the remaining catalyst was carried out in the manner of Example 1, with the result that there was no contamination of catalyst observed.

What we claim is:

1. In a method for producing a polymer or copolymer of lactic acid and/or glycolic acid by subjecting lactic acid and/or glycolic acid to a polycondensation reaction, an improvement which comprises employing a solid inorganic acid catalyst as a polycondensation catalyst, wherein the solid inorganic acid catalyst is one selected from the group consisting of acid clay, activated clay, bentonite, kaolin, talc, aluminum silicate, magnesium silicate, alumina bolia and silicic acid.

2. A method as claimed in claim 1, wherein the weight-average molecular weight of the polymer or copolymer is about not less than 5,000 and a dispersity of it is about 1.5 to 2.

3. A method as claimed in claim 1, wherein the weight-average molecular weight of the polymer or copolymer is about 5,000 to 30,000 and a dispersity of it is about 1.5 to 2.

4. A method in claim 1, wherein the polymer consists of lactic acid unit.

5. A method as claimed in claim 1, wherein the copolymer consists of lactic acid and glycolic acid units.

6. A method as claimed in claim 5, wherein the copolymer ratio is about 50 to 95 weight % of lactic acid and about 50 to 5 weight % of glycolic acid.

7. A method as claimed in claim 5, wherein the copolymer ratio is about 60 to 95 weight % of lactic acid and about 40 to 5 weight % of glycolic acid.

8. A method as claimed in claim 5, wherein the copolymer ratio is about 60 to 85 weight % of lactic acid and about 40 to 15 weight % of glycolic acid.

9. A method as claimed in claim 5, wherein the copolymer ratio is about 75±2 mol % of lactic acid and about 25±2 mol % of glycolic acid.

10. A method as claimed in claim 1, wherein the solid inorganic acid catalyst is one selected from the group consisting of acid clay, activated clay, kaolin, bentonite and aluminium silicate.

11. A method as claimed in claim 1, wherein the solid inorganic acid catalyst is acid clay.

12. A method as claimed in claim 1, wherein the solid inorganic acid catalyst is activated clay.

13. A method as claimed in claim 1, wherein the solid inorganic acid catalyst is aluminium silicate.

* * * * *

UNITED STATES PATENT AND TRADEMARK OFFICE
CERTIFICATE OF CORRECTION

PATENT NO. : 4,683,288

DATED : July 28, 1987

INVENTOR(S) : Motoaki TANAKA et al.

It is certified that error appears in the above-identified patent and that said Letters Patent is hereby corrected as shown below:

On the first page of the patent, "Assignees"

should read --Wako Pure Chemical Industries,

Ltd. and Takeda Chemical Industries, Ltd., both of Osaka, Japan--

Signed and Sealed this

Ninth Day of February, 1988

*Attest:*

DONALD J. QUIGG

*Attesting Officer*  *Commissioner of Patents and Trademarks*